(12) United States Patent
Kim et al.

(10) Patent No.: US 8,434,935 B2
(45) Date of Patent: May 7, 2013

(54) HEATING FURNACE FOR TESTING MIDDLE AND LONG SPAN STRUCTURES

(75) Inventors: Heung Youl Kim, Seoul (KR); Bong Jae Lee, Seoul (KR); Hyung Jun Kim, Gyeonggi-do (KR)

(73) Assignee: Korea Institute of Construction Technology, Gyeonggi-do (KR)

( * ) Notice: Subject to any disclaimer, the term of this patent is extended or adjusted under 35 U.S.C. 154(b) by 273 days.

(21) Appl. No.: 12/941,255

(22) Filed: Nov. 8, 2010

(65) Prior Publication Data

US 2011/0110393 A1    May 12, 2011

(30) Foreign Application Priority Data

Nov. 10, 2009  (KR) .................. 10-2009-0108279

(51) Int. Cl.
*G01N 25/00* (2006.01)
*G01K 17/00* (2006.01)
*G01K 3/00* (2006.01)

(52) U.S. Cl.
USPC ........ 374/8; 374/31; 374/208; 374/5; 374/57; 374/51; 374/141

(58) Field of Classification Search ............... 374/8, 31, 374/208, 5, 57, 51, 141
See application file for complete search history.

(56) References Cited

U.S. PATENT DOCUMENTS

| | | | | |
|---|---|---|---|---|
| 2,745,280 | A | * | 5/1956 | Conaway .................. 374/52 |
| 3,310,979 | A | * | 3/1967 | Hall .................. 73/844 |
| 3,369,390 | A | * | 2/1968 | Chu et al. .................. 374/52 |
| 3,593,563 | A | * | 7/1971 | Marmor et al. .................. 374/8 |
| 3,908,440 | A |   | 9/1975 | Houser |
| 5,015,825 | A |   | 5/1991 | Brindley |
| 6,991,365 | B1 | * | 1/2006 | Pierorazio .................. 374/8 |
| 2005/0117625 | A1 | * | 6/2005 | Ogle et al. .................. 374/141 |
| 2008/0267252 | A1 | * | 10/2008 | West et al. .................. 374/45 |

\* cited by examiner

FOREIGN PATENT DOCUMENTS

JP          04265837 A  *  9/1992

OTHER PUBLICATIONS

Chan-Wei Wu et al, "Fire Resistance Tests of a Glass Pane With Down-Flowing Water Film", Journal of the Chinese Institute of Engimeers, vol. 31, No. 5, issued on Jul. 5, 2008, p. 737-p. 744.

*Primary Examiner* — Mirellys Jagan
(74) *Attorney, Agent, or Firm* — J.C. Patents

(57) ABSTRACT

A heating furnace for testing middle and long span structures including a modular partition structure to adjust an inner volume of the heating furnace, effectively performing a load-coupled heating test of full scale members such as a beam, a short column, a slab, a conjunction frame, and a deck plate. The heating furnace for testing middle and long span structures includes a partition unit formed of a refractory material and partitioning a heating space in a main body to block transfer of heat generated from one space to the other space. A test sample is installed in the heating space of the main body partitioned by the partition unit according to a size of the test sample, and then, heat and a compression force are applied to the test sample to perform a fireproof performance test. The fireproof performance test of structure members having various lengths of 4 m, 6 m and 10 m can be performed, and consumption of various utilities consumed during the test can be optimized. In addition, since the heating furnace can perform an actual material test of full scale structures such as continuous span beams and long span beams, deck plates, or bridge trusses of civil structures, deck plates for ships, and so on, target fireproof performance estimation of various shape conditions can be performed to increase applicability of the test.

4 Claims, 7 Drawing Sheets

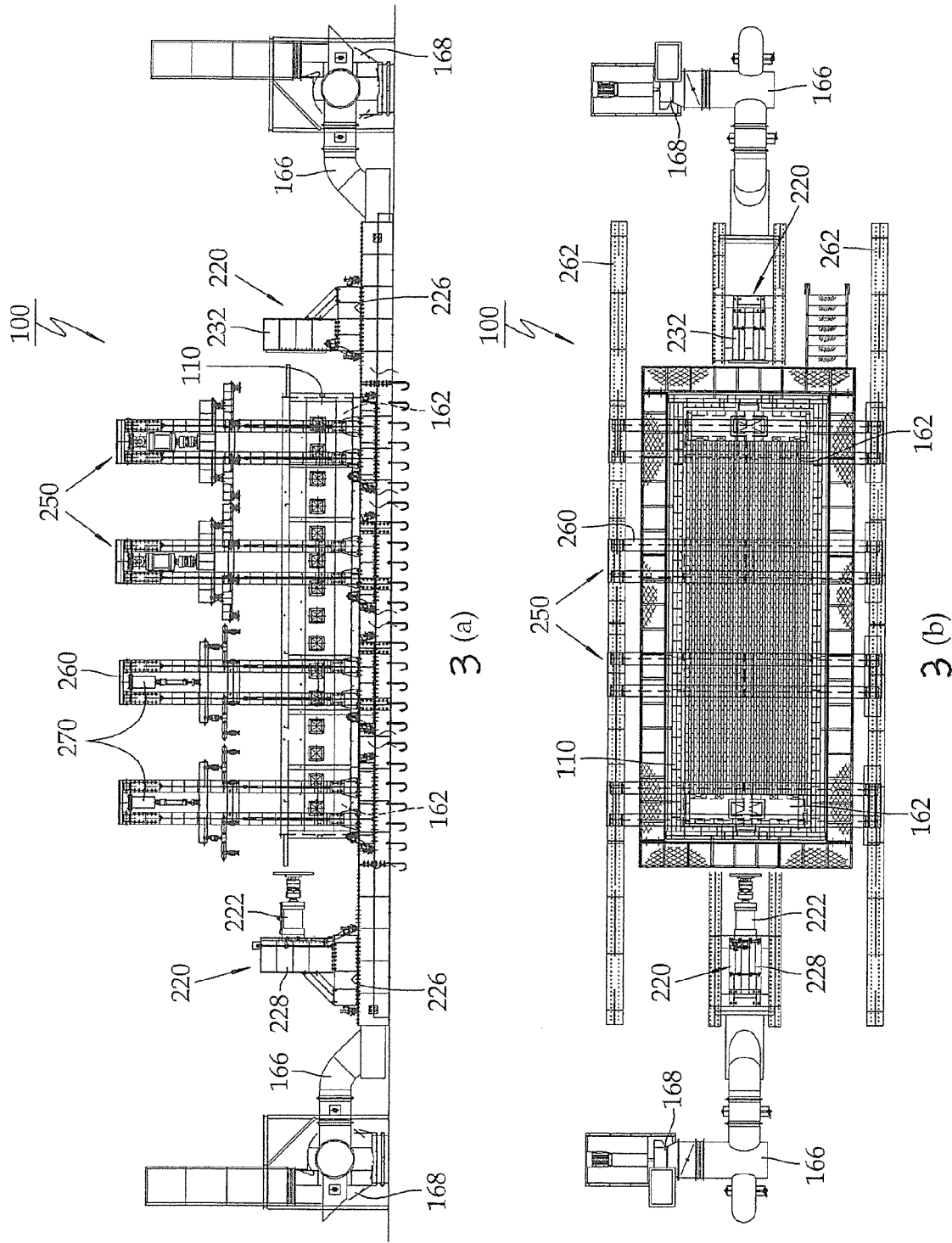

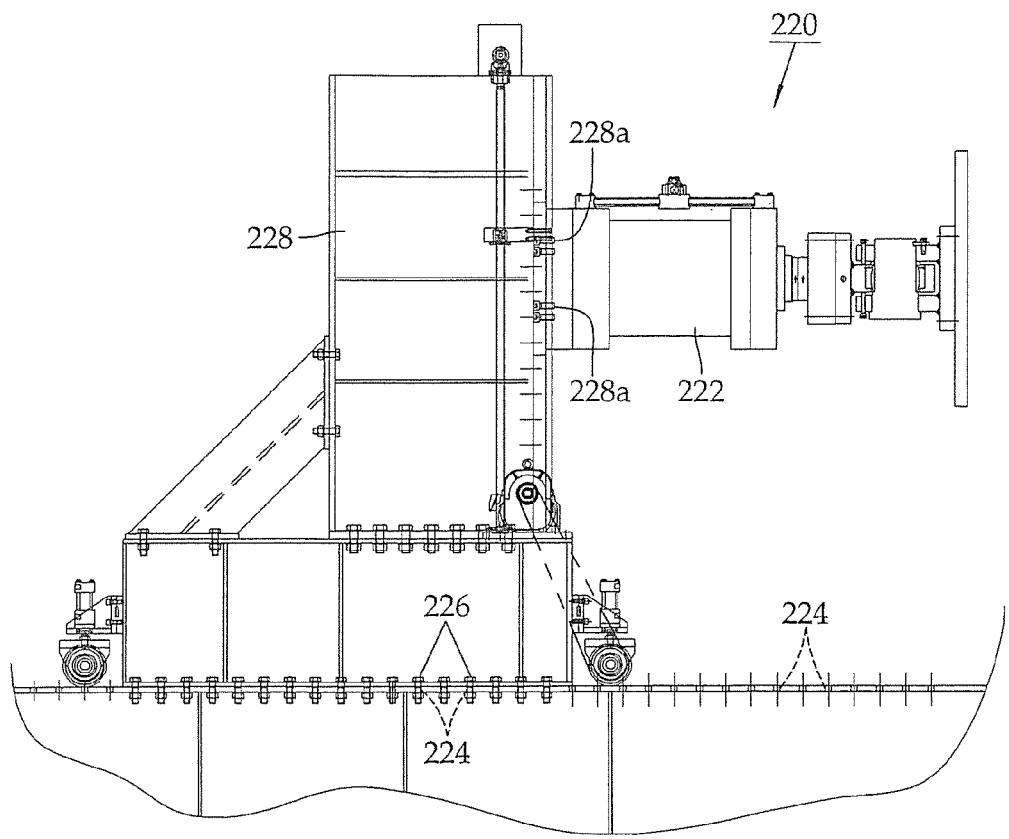
4-(a)
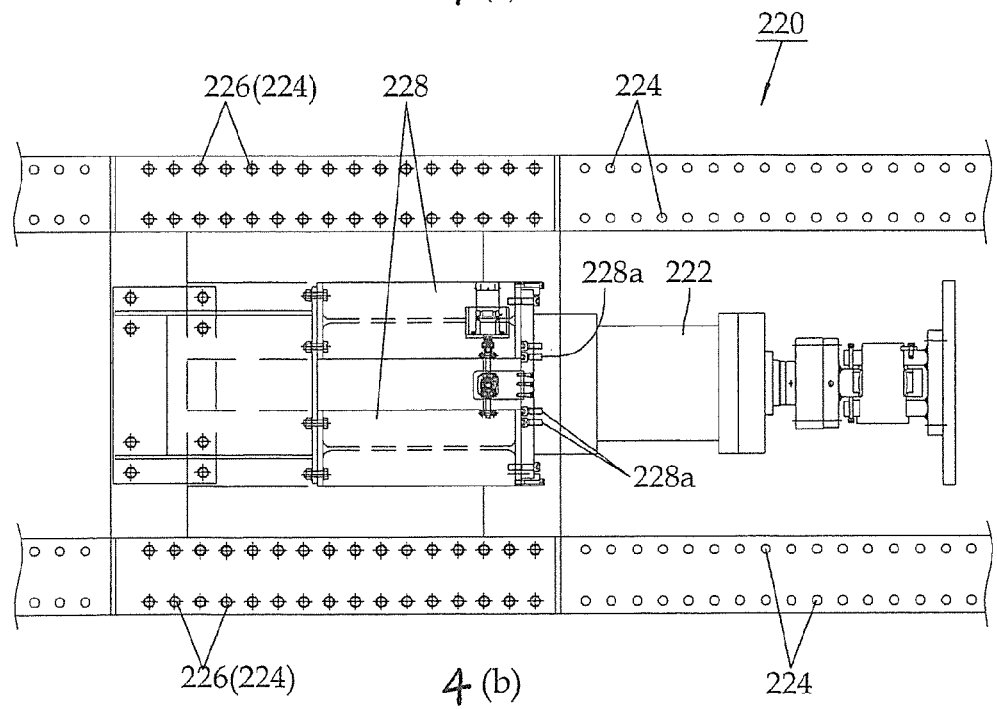
4-(b)

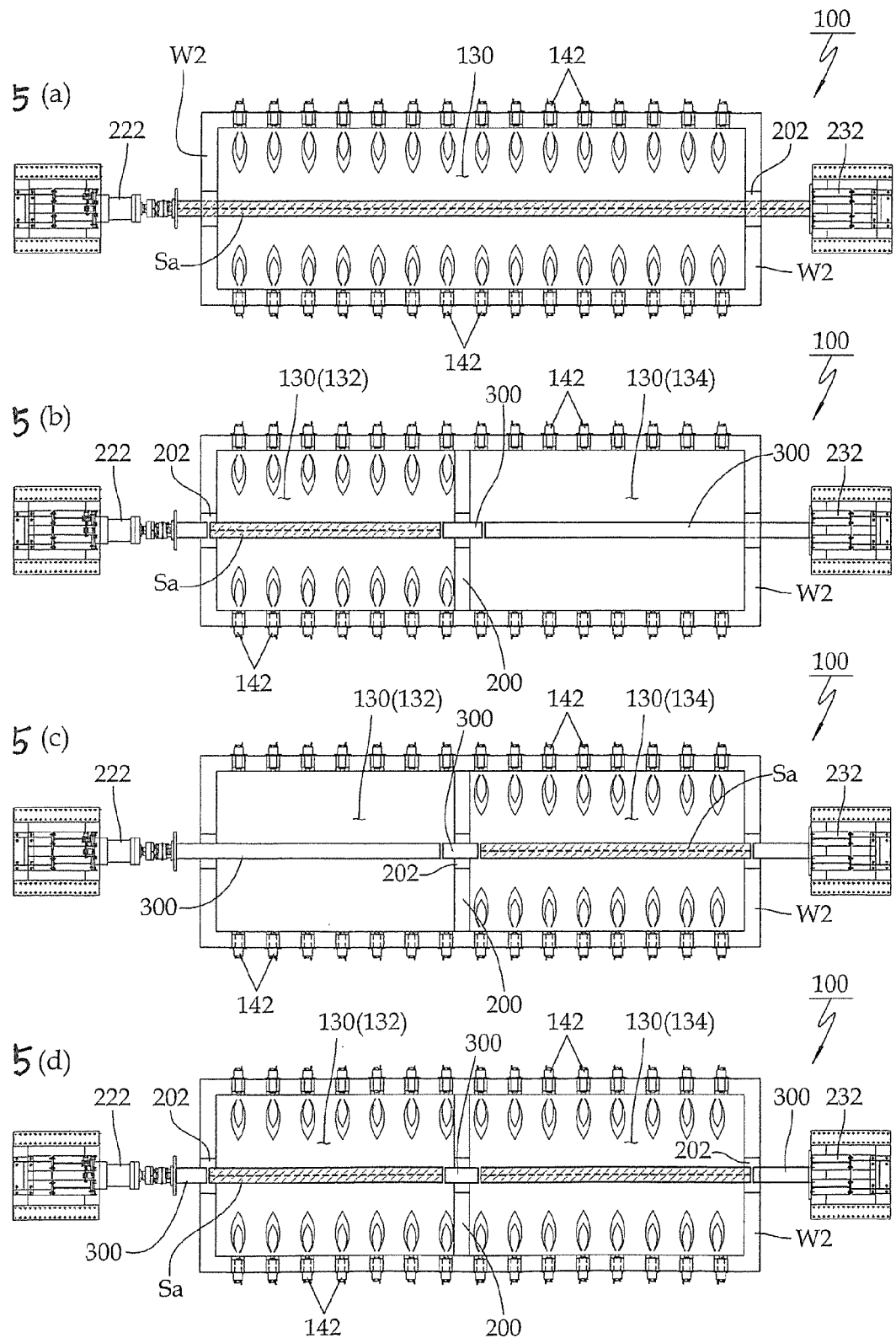

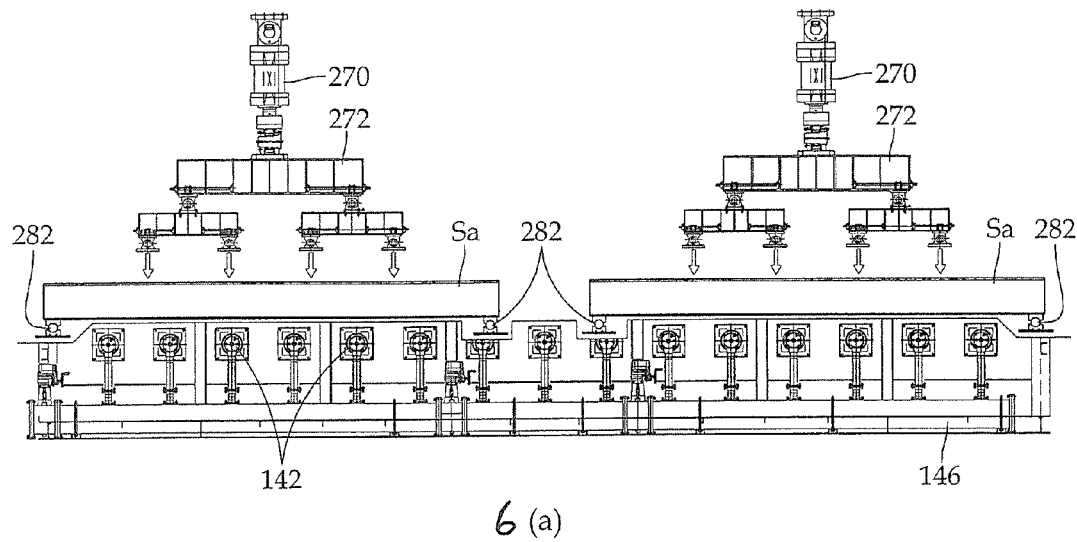
6 (a)
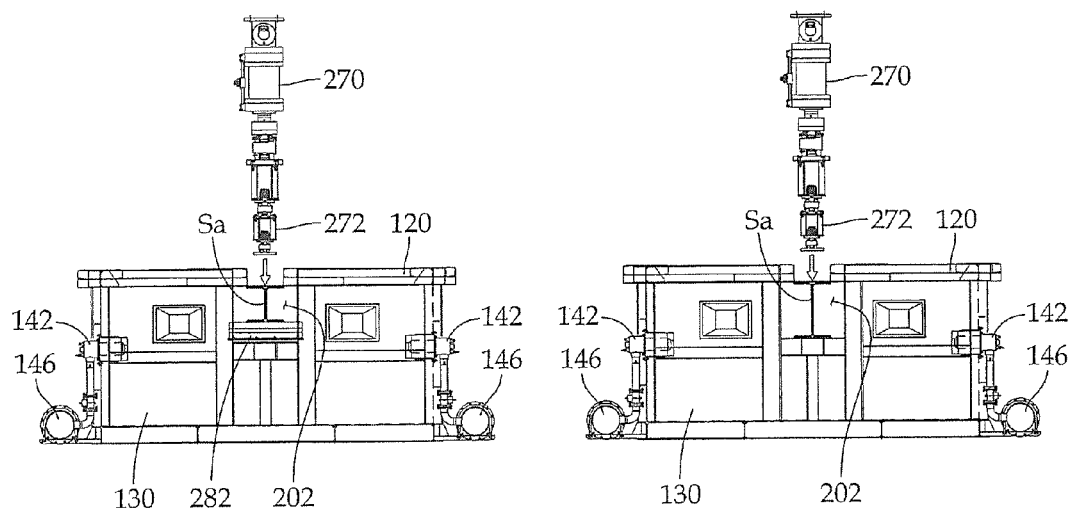
6 (b)

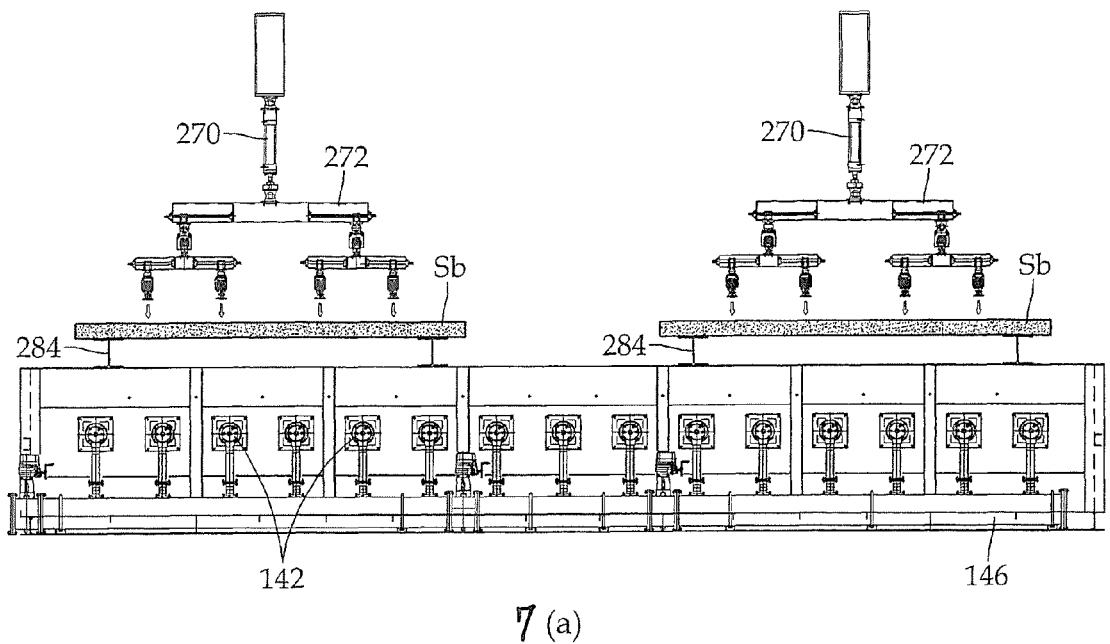
7 (a)
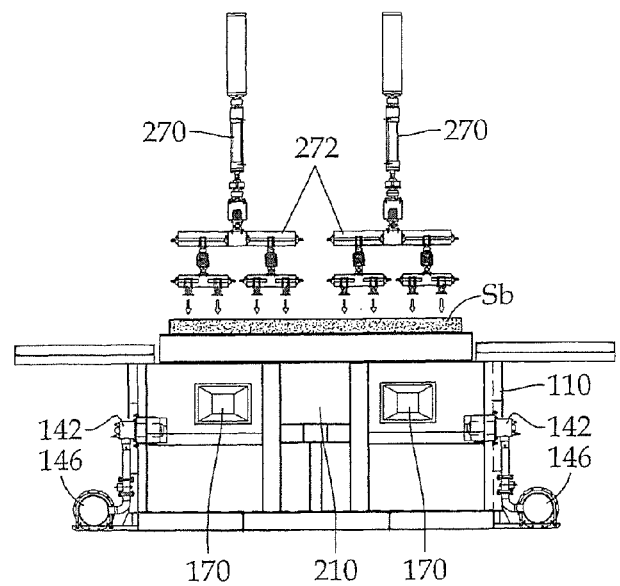
7 (b)

HEATING FURNACE FOR TESTING MIDDLE AND LONG SPAN STRUCTURES

CROSS-REFERENCE TO RELATED APPLICATION

This application claims the priority benefits of Korea patent application serial no. 10-2009-0108279, filed on Nov. 10, 2009. The entirety of the above-mentioned patent applications is hereby incorporated by reference herein and made a part of specification.

BACKGROUND

1. Field

The present invention relates to a heating furnace for heating middle and long span structures of a construction structure to perform a structure test and a fireproof performance test, and more particularly, to a heating furnace for testing middle and long span structures including a modular partition structure for adjusting an inner volume according to sizes of middle and long span members used in a high-rise and large-space building to check a full scale fireproof performance and extract a scale factor of the middle and long span members and enabling an effective load-coupled heating test of the middle and long span members such as a beam, a short column, a slab, a conjunction frame, a deck plate, a deck plate for a ship, and so on.

2. Description of the Related Art

In recent times, due to development of industries, concentration of population and urbanization, buildings are undergoing Manhattanization and becoming larger and larger. Thus, if a building is on fire, the fire may easily become out of control and cause serious material damage and casualties.

When the building is on fire, a structural member is exposed to a large amount of heat and is structurally weakened, making it unable to maintain its structural strength. Accordingly, when the building is on fire, the strength of the structure is decreased, causing the building to easily collapse, which frequently results in serious casualties and property damage.

Since use performance limits or structural destruction of the structural member affected by the large amount of heat upon fire of the construction structure are determined according to support conditions, load states and fire-exposed surfaces as well as physical and thermal characteristics of a material constituting the building structure, it is important to perform fireproof design of the structure in consideration of this.

In the conventional art related thereto, tests of applying heat to a short structural member and measuring strength thereof have been frequently performed. For example, Korean Patent Laid-open Publication No. 10-2008-011450, entitled "EQUIPMENT FOR TESTING SPALLING FAILURE OF CONCRETE UNDER CONDITION OF APPLYING LOAD," discloses an apparatus for performing a concrete explosive spalling test under a load applying condition.

As shown in FIG. 1, a conventional concrete explosive spalling test apparatus 1 under a load applying condition includes a heating furnace body 30 having one surface on which a sample 10 is disposed, a heating assembly 50 for supplying flame to the heating furnace body 30, a load applying assembly 60 for forming a load applying condition to the sample 10, and a controller 70 for controlling the heating assembly 50 according to pre-input fire conditions. Since the conventional concrete explosive spalling test apparatus 1 under a load applying condition can perform fire tests of samples in a load applying condition, explosive spalling tests according to various fire conditions may be performed. In addition, since the heating assembly is controlled on the basis of temperature data measured by a plurality of temperature sensors, the tests can be accurately performed.

However, the conventional test apparatus can only perform a load-coupled heating test of samples such as a simple concrete block having a short length, but cannot perform fireproof performance tests of various full scale members such as middle and long span members used in a high-rise and large-space building, for example, middle and long span beams having lengths of 4 m, 6 m and 10 m, short columns, slabs, conjunction frames, deck plates, deck plates for a ship, and so on.

SUMMARY

In order to solve the problems, the present invention is directed to a heating furnace for testing middle and long span structures capable of easily performing a fireproof performance test of various full scale members such as middle and long span members used in a high-rise and large-space building, for example, middle and long span beams having lengths of 4 m, 6 m and 10 m, short columns, slabs, conjunction frames, deck plates, deck plates for a ship, and so on.

In addition, the present invention is also directed to a heating furnace for testing middle and long span structures having a modular structure that can easily adjust an inner volume of the heating furnace according to sizes of middle and long span structures during a load-coupled heating test, optimizing consumption of various utilities required for the test and performing various fireproof performance tests.

According to an exemplary aspect, there is provided a heating furnace for testing middle and long span structures, which includes: a main body having an inner wall formed of a refractory material and an outer wall formed of a steel material, a detachable cover installed on an open upper part thereof, and a heating space formed therein; a heating unit including a burner for providing heat from both sidewalls of the main body to heat the heating space; an exhaust unit having a plurality of exhaust ports for discharging an exhaust gas in the heating space from both sidewalls in a widthwise direction of the main body, and exhaust pipes connected to the exhaust ports to discharge the exhaust gas to a chimney, respectively; a partition unit for partitioning the heating space of the main body and formed of a refractory material to block transfer of heat generated from one space to the other space; a horizontal force applying unit including a horizontal actuator for applying a compression force to one side of a test sample installed in a longitudinal direction of the main body, and a reaction frame for supporting the other side of the test sample at an opposite side of the horizontal actuator; and a vertical force applying unit including a vertical actuator for applying a compression force to the test sample from an upper part of the test sample installed in the main body, and a support frame for supporting the test sample on the main body, wherein the heating space of the main body is partitioned using the partition unit to correspond to a size of the test sample, and heat and a compression force are applied to the test sample in the heating space to perform a fireproof performance test.

Therefore, the fireproof performance test can be easily performed with respect to the middle and long span members used in a high-rise and large-space building, and an inner volume of the heating furnace can be easily adjusted, optimizing consumption of various utilities required for the test and variously performing the fireproof performance test.

In addition, a test sample mounting space is formed at the both sidewalls in the widthwise direction of the main body and an upper center of the partition unit, and a blocking wall formed of a refractory material is disposed in the test sample mounting space to open the test sample mounting space according to the size of the test sample, performing the fireproof performance test. The test sample having various sizes to a height of 800 mm can be mounted in the heating space to perform the fireproof performance test through the test sample mounting space and the blocking wall.

Further, the support frame of the vertical force applying unit may include a movable beam support installed on the bottom to support both ends of a linear test sample installed in the heating furnace, and a plate support mounted on an upper center of the main body, in which the cover is opened, to support a plate-shaped test sample. Therefore, it is possible to perform the fireproof performance test of a full scale test of middle and long span beams, a short column, a slab, a conjunction frame, a deck plate, a deck plate for a ship, and so on.

Furthermore, the partition unit may be removed from the interior of the heating space of the main body, the test sample may be mounted to cross the heating space, the heating unit may operate the burner throughout the heating space, and the exhaust unit may exhaust an exhaust gas through a plurality of exhaust ports so that the test sample is heated and compressed to perform a fireproof performance test. Therefore, it is possible to easily perform the fireproof performance test of the long span test sample having a length of 10 m.

In addition, a test sample may be mounted in a first space of the main body partitioned by the partition unit, the heating unit may operate the burner disposed in the first space, and the exhaust unit may exhaust an exhaust gas through the exhaust ports disposed in the first space so that the test sample is heated and compressed to perform a fireproof performance test. Therefore, it is possible to easily perform the fireproof performance test of the middle and long span test samples having lengths of 4 m and 6 m, without excessive consumption of utilities.

Further, a test sample may be mounted in a second space of the main body partitioned by the partition unit, the heating unit may operate the burner disposed in the second space, and the exhaust unit may exhaust an exhaust gas through the exhaust ports disposed in the second space so that the test sample is heated and compressed to perform a fireproof performance test. Therefore, it is possible to easily perform the fireproof performance test of the middle and long span test samples having lengths of 4 m and 6 m, without excessive consumption of utilities.

Furthermore, a plurality of test samples may be mounted in a first space and a second space of the main body partitioned by the partition unit, the heating unit may operate the burner disposed in the first and second spaces, and the exhaust unit may exhaust an exhaust gas through one exhaust port disposed in the first space and the other exhaust port disposed in the second space so that the plurality of test samples are heated and compressed to perform a fireproof performance test. Therefore, it is possible to more effectively perform the fireproof performance test of the plurality of middle and long span test samples.

In addition, the first space may have a heating space of a length of 4 m so that a linear test sample or a plate-shaped test sample having a length of 4 m can be tested, and the second space may have a heating space of a length of 6 m so that a linear test sample or a plate-shaped test sample having a length of 6 m can be tested. As described above, it is possible to easily perform the fireproof performance test of the middle and long span test samples having various sizes and shapes.

Further, the horizontal actuator and the reaction frame of the horizontal force applying unit may be assembled along a plurality of threaded holes formed at the bottom by bolts to be laterally position-adjusted with respect to the heating space of the main body, and the horizontal actuator may be vertically height-adjusted on an upright frame. Therefore, it is possible to easily apply a horizontal compression force and perform the fireproof performance test of the middle and long span test samples having various sizes and shapes.

Furthermore, the vertical force applying unit may be is movable on rails disposed at both sides of the bottom of the main body so that the vertical actuator is movable in the longitudinal direction of the main body. Therefore, it is possible to easily apply a horizontal compression force and perform the fireproof performance test of the middle and long span test samples having various lengths and sizes.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the aspects of the invention.

FIG. 3A is a side view of the entire structure of the heating furnace for testing middle and long span structures in accordance with an exemplary embodiment of the present invention.

FIG. 3B is a plan view of the entire structure of the heating furnace for testing middle and long span structures in accordance with an exemplary embodiment of the present invention.

FIG. 4A is a side view of a horizontal actuator of a horizontal force applying means provided in the heating furnace for testing middle and long span structures in accordance with an exemplary embodiment of the present invention.

FIG. 4B is a plan view of the horizontal actuator of the horizontal force applying means provided in the heating furnace for testing middle and long span structures in accordance with an exemplary embodiment of the present invention.

FIG. 5A is a view for explaining a fireproof performance test using the horizontal force applying means in a state in which a long span linear test sample having a length of 10 m is mounted in the heating furnace for testing middle and long span structures in accordance with an exemplary embodiment of the present invention.

FIG. 5B is a view for explaining a fireproof performance test using the horizontal force applying means in a state in which a middle and long span linear test sample having a length of 4 m is mounted in a first space of the heating furnace for testing middle and long span structures in accordance with an exemplary embodiment of the present invention.

FIG. 5C is a view for explaining a fireproof performance test using the horizontal force applying means in a state in which a middle and long span linear test sample having a length of 6 m is mounted in a second space of the heating furnace for testing middle and long span structures in accordance with an exemplary embodiment of the present invention.

FIG. 5D is a view for explaining a fireproof performance test using the horizontal force applying means in a state in which a plurality of middle and long span linear test samples are mounted in the first and second spaces of the heating furnace for testing middle and long span structures in accordance with an exemplary embodiment of the present invention.

FIG. 6A is a side view showing a fireproof performance test using the horizontal force applying means in a state in which a plurality of linear test samples are mounted in the first and second spaces of the heating furnace for testing middle and long span structures in accordance with an exemplary embodiment of the present invention.

FIG. 6B is a cross-sectional view showing a fireproof performance test using the horizontal force applying means in a state in which a linear test sample is mounted in a test sample mounting space of the heating furnace for testing middle and long span structures in accordance with an exemplary embodiment of the present invention.

FIG. 7A is a side view showing a fireproof performance test using the horizontal force applying means in a state in which a plurality of plate-shaped test samples are mounted in the first and second spaces of the heating furnace for testing middle and long span structures in accordance with an exemplary embodiment of the present invention.

FIG. 7B is a cross-sectional view showing a fireproof performance test using the horizontal force applying means in a state in which a plate-shaped test sample is mounted in the heating furnace for testing middle and long span structures in accordance with an exemplary embodiment of the present invention.

DETAILED DESCRIPTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

Figure 1:
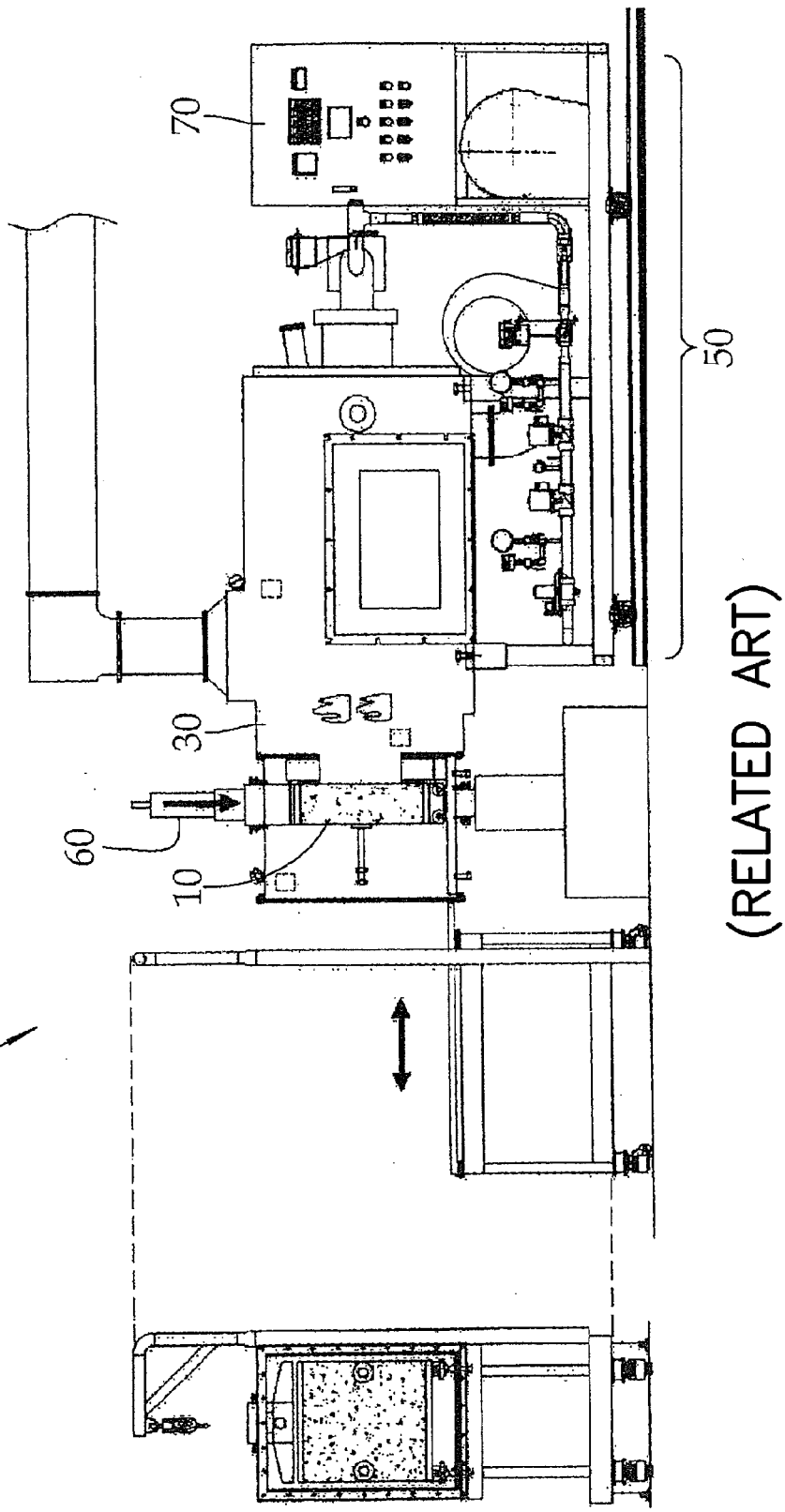
FIG. 1 is a side view of a conventional concrete explosive spalling test apparatus under a load applying condition.
Figure 2:
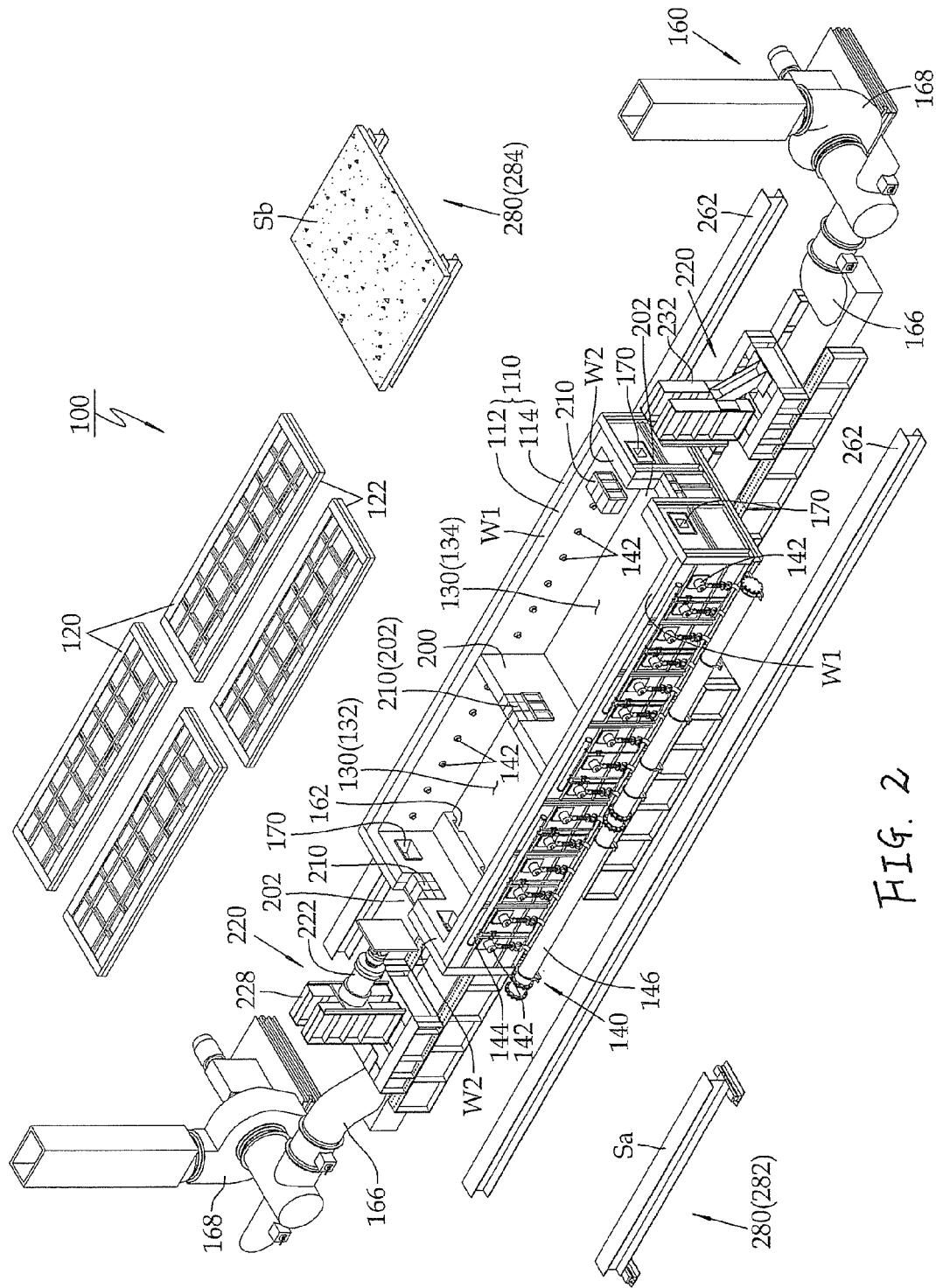
FIG. 2 is an exploded perspective view of a heating furnace for testing middle and long span structures in accordance with an exemplary embodiment of the present invention.

As fully shown in FIG. 2, a heating furnace 100 for testing middle and long span structures in accordance with the present invention includes a main body 110 constituted by an inner wall 112 formed of a refractory material and an outer wall 114 formed of a steel material. The main body 110 includes a detachable cover 120 to open an upper part thereof, and a heating space 120 provided therein.

The cover 120 covered on the main body 110 is formed of a steel structure having a refractory material applied on one surface thereof, which may be provided in plural. In addition, a heating means 140 is disposed in the main body 110 to provide heat from both sidewalls w1 in a longitudinal direction thereof to heat the heating space 130.

The heating means 140 includes a plurality of burners 142 in which LPG or LNG is used as fuel. The burners 142 are installed opposite each other at middle positions of both sidewalls w1 in a longitudinal direction of the main body 110.

A gas pipe 144 for supplying LPG or LNG to the burners 142 of the heating means 140 and an air supply pipe 146 for supplying combustion air are installed at outer surfaces of the both sidewalls w1 in the longitudinal direction of the main body 110.

In addition, an exhaust means 160 for discharging a combustion gas generated from the burners 142 of the heating means 140, i.e., an exhaust gas, to the exterior is provided. The exhaust means 160 includes a plurality of exhaust ports 162 for discharging an exhaust gas in the heating space 130 from lower parts of both sidewalls w2 in a widthwise direction of the main body 110 to the exterior. The respective exhaust ports 162 are connected to exhaust pipes 166 to be discharged to a chimney (not shown).

That is, the exhaust means 160 partially discharges the exhaust gas through a lower part of the main body 110 by partitioning the heating space 130 of the main body 110 from the lower part of the both sidewalls w2 in the widthwise direction of the main body 110 using the respective exhaust ports 162, rather than simply discharging the exhaust gas generated in the main body 110 of the heating furnace 100 to the exterior. The exhaust means 160 includes blowers 168 respectively installed at the exhaust pipes 166, and the plurality of discharge ports 162 may be separately operated.

In addition, a plurality of sight glasses 170 are installed at the both sidewalls w2 in the widthwise direction of the main body 110 so that a combustion state in the heating space 130 of the main body 110 can be observed with the naked eye.

Further, the heating furnace 100 for testing middle and long span structures in accordance with the present invention includes a partition means 200 for partitioning the heating space 130 of the main body 110 into first and second spaces 132 and 134.

The partition means 200 functions to prevent heat generated from one space from being transferred to the other space using a refractory material. The partition means 200 may be extracted from the heating space 130 of the main body 110. The partition means 200 has a modular structure in which the heating space 130 of the main body 110 is partitioned into a first space 132 having a length of 4 m and a second space 134 having a length of 6 m.

Therefore, the main body 110 is partitioned into a plurality of spaces by the partition means 200, and a test sample mounting space 202 is formed at center parts of upper parts of the both sidewalls w2 in the widthwise direction of the main body 110 and the partition means 200. A blocking wall 210 formed of a refractory material is positioned at the test sample mounting space 202 to open the test sample mounting space 202 according to a size of a test sample.

That is, the blocking wall 210 has a detachable assembly structure to open the test sample mounting space 202 according to the size of the test sample disposed in the test sample mounting space 202. When the space 202 is completely opened, the test sample having a height of 800 mm or less can be disposed in the test sample mounting space 202 to enter the heating space 130, performing the fireproof performance test.

In addition, the heating furnace 100 in accordance with the present invention includes a horizontal force applying means 220 disposed at an outer side of the main body 110. As shown in FIGS. 3A and 3B, the horizontal force applying means 220 includes a horizontal actuator 222 for applying a compression force to one side of the test sample installed in the longitudinal direction of the main body 110, and a reaction frame disposed at an opposite side of the horizontal actuator 222 and supporting the other side of the test sample.

Further, as shown in FIGS. 4A and 4B, the horizontal force applying means 220 has a structure in which the horizontal actuator 222 and the reaction frame 232 are assembled along a plurality of threaded holes 224 formed in the bottom by bolts 226, enabling position adjustment of the horizontal force applying means 220 with respect to the heating space 130 of the main body 110. That is, when the horizontal actuator 222 and the reaction frame 232 are moved along the plurality of threaded holes 224 and then assembled by the bolts 226, the position thereof can be adjusted to be near or far from the main body 110 of the heating furnace 100 according to the length and size of the test sample.

Here, the horizontal actuator 222 is configured to be vertically height-adjusted on an upright frame 228. When the horizontal actuator 222 is fixed on the upright frame 228 formed of a steel structure by bolts 228a, a horizontal compression force can be easily applied to the middle and long span test samples having various sizes and shapes to perform a fireproof test.

In addition, the heating furnace 100 for testing middle and long span structures in accordance with the present invention includes a vertical force applying means 250 for applying a compression force to a test sample from an upper part of the test sample installed at the main body 110.

As shown in FIGS. 3A and 3B, the vertical force applying means 250 includes a vertical actuator 270 vertically installed on a gantry-type crane 260, and a support frame 280 for supporting a test sample on the main body 110 as shown in FIG. 2.

In the vertical force applying means 250, the gantry-type crane 260 can move along rails 262 disposed on both bottoms of the main body 110 to move the vertical actuator 270 in a longitudinal direction of the main body 110.

The vertical force applying means 250 functions to apply a vertical compression force to a full scale member such as middle and long span beams, short columns, slabs, conjunction frames, deck plates, deck plates for a ship, and so on. As shown in FIG. 6, various clamps 272 may be mounted on the vertical actuator 270 to variously apply a vertical compression force to the test sample.

The test sample that can pass through the fireproof performance test of the present invention includes a linear test sample Sa such as a beam, a column, or a frame, and a plate-type test sample Sb such as a slab, a deck plate, or a deck plate for a ship.

Meanwhile, as shown in FIGS. 2, 6A and 6B, the support frame 280 provided in the vertical force applying means 250 includes a movable beam support 282 for supporting both ends of the linear test sample Sa installed in the heating furnace 100, and a plate support 284 mounted on an upper center part of the main body 100 in which the cover 120 is opened, to support the plate-type test sample Sb.

As described above, the vertical force applying means 250 can use the vertical actuator 270 and the support frame 280 to variously test the linear test sample Sa having a column shape such as middle and long span beams, a short column and a conjunction frame, and the plate-type test sample Sb such as a slab, a deck plate, or a deck plate for a ship.

Hereinafter, a method of performing a fireproof performance test of various test samples using a heating furnace 100 for testing middle and long span structures in accordance with the present invention will be exemplarily described.

The heating furnace 100 for testing middle and long span structures in accordance with the present invention can partition the heating space 130 of the main body 110 using the modular partition means 200 according to the size of the test sample, install the test sample in the corresponding heating space 130, and apply heat and compression force to the heating space 130, effectively performing the fireproof performance test.

For example, as shown in FIG. 5A, a fireproof performance test of a long span linear test sample having a length of 10 m can be easily performed.

In the fireproof performance test, the partition means 200 is removed from the interior of the heating space 130 of the main body 110, the test sample is mounted to cross the heating space 130 to be disposed between the horizontal actuator 222 and the reaction frame 232, and then, the cover 120 is covered on the main body 110.

At this time, as shown in the cross-sectional view of FIG. 6B, the linear test sample Sa is disposed in the test sample mounting space 202 formed at both sidewalls w2 in the widthwise direction of the main body 110. Here, an opening size of the blocking wall 210 is varied depending on the height of the test sample.

In addition, the burners 142 of the heating means 140 are operated through the entire heating space 130 of the main body 110, and the exhaust means 160 exhausts an exhaust gas through the plurality of exhaust ports 162 to rapidly heat the test sample for a short time through a desired temperature pattern, for example, KS or ISO Fire Test, IMO Ship Test method, or Tunnel Fire Test Method (RWS/RABT/MHC FIRE). After reaching a desired temperature, the horizontal actuator 222 is operated to compress the test sample, performing the fireproof performance test. Accordingly, it is possible to easily perform the fireproof performance test of the long span linear test sample Sa having a length of 10 m.

Further, unlike the above, for example, as shown in FIG. 5B, a fireproof performance test of a middle and long span linear test sample Sa having a length of 4 m can be easily performed. In the above fireproof performance test, the linear test sample Sa is installed in the first space 132 of the main body 110 partitioned by the partition means 200 and disposed between the horizontal actuator 222 and the reaction frame 232, and the cover 120 is covered on the first space 132 of the main body 110. At this time, an auxiliary compression frame 200 is installed at the second space 134, in which no test sample is disposed, to extend to the reaction frame 232 so that the test sample can be compressed between the horizontal actuator 222 and the reaction frame 232.

Furthermore, the burners 142 of the heating means 140 are operated to only the first space 132 of the main body 110, and the exhaust means 160 exhausts an exhaust gas through the exhaust ports 162 disposed at the first space 132 to simultaneously compress the test sample, performing the load-coupled heating fireproof test. In addition, when the test sample S arrives at the desired temperature according to the set temperature pattern, the test sample S is compressed to perform the fireproof performance test. In this case, since the burners 142 disposed at the second space 134 of the main body 110 are not operated and the exhaust ports 162 are not operated either, the fireproof performance test can be easily performed without excessive consumption of utilities.

Similarly, as shown in FIG. 5C, the linear test sample Sa is mounted in the second space 134 of the main body 110 partitioned by the partition means 200, and the fireproof performance test of the middle and long span structure having a length of 6 m can be performed through the same method as described above without excessive consumption of utilities.

In addition, as shown in FIG. 5D, a plurality of linear test samples Sa are mounted in the first space 132 and the second space 134 partitioned by the partition means 200 to be tested. In this case, when the test sample having a length of 4 m is installed in the first space 132 and the test sample having a length of 4 m is installed in the second space 134, a space of 2 m remains in the center part. When the test is performed in a state partitioned into both parts, a horizontal load test is not performed, and a vertical load or heating test is mainly performed.

Of course, in a specific case in which the horizontal load test is needed, a horizontal extension clamp 300 may be installed at the center part of 2 m.

In this case, the heating means 140 operates all the burners 142 disposed in the first space 132 and the second space 134 to simultaneously heat the plurality of test samples, and the exhaust means 160 exhausts an exhaust gas through one exhaust port 162 disposed in the first space 132 and the other exhaust port 162 disposed in the second space 134.

In addition, the horizontal actuator 222 is operated with respect to the test samples to check stability of the test samples for a predetermined time before the heating test, and then, the test samples are simultaneously compressed to a desired temperature and time according to a set temperature and time pattern to perform the load-coupled heating fireproof performance test. In addition, when the test sample arrives at a desired temperature according to the set temperature pattern, the horizontal actuator 222 is operated to simultaneously compress the plurality of linear test samples Sa, performing the load-coupled heating fireproof performance test. Therefore, fireproof performance tests of the plurality of middle and long span test samples can be effectively and simultaneously performed.

Meanwhile, the heating furnace 100 for testing middle and long span structures in accordance with the present invention can easily apply a vertical compression force to the middle and long span linear test samples Sa having various lengths to perform the fireproof performance test.

For example, as shown in FIGS. 6A and 6B, the vertical compression force can be easily applied to the middle and long span linear test samples Sa having various sizes to perform the fireproof performance test. In this case, for example, the plurality of linear test sample Sa can be mounted and tested in the first space 132 and the second space 134 partitioned by the partition means 200.

At this time, as shown in the cross-sectional view of FIG. 6B, the test sample is disposed in the test sample mounting space 202 formed on the both sidewalls w2 in the widthwise direction of the main body 110 and the partition means 200. Here, an opening size of the blocking wall 210 is varied depending on the height of the test sample.

In addition, as shown in FIG. 2, beam supports 282 are installed at both ends of the test sample. The beam supports 282 are installed at the bottom of the heating furnace to support both ends of the linear test samples disposed in the first space 132 and the second space 134 of the main body 110.

In this case, the cover 120 is covered on the first space 132 and the second space 134 of the main body 110, the linear test sample Sa is disposed just under the cover 120 to expose an upper surface thereof to the exterior, and both corners of the upper surface are in close contact with lower end corners of the cover 120, so that three lower surfaces of the linear test sample Sa are exposed to the first space 132 and the second space 134.

In this state, the heating means 140 operates all the burners disposed in the first space 132 and the second space 134 to simultaneously heat the plurality of test samples, and the exhaust means 160 exhausts an exhaust gas through the one exhaust port 162 disposed in the first space 132 and the other exhaust port 162 disposed in the second space 134.

Through the above disposition, the three surfaces of the test sample are heated, and heat is remained in the first space 132 and the second space 134 by the cover 120, rather than being discharged to the exterior. In addition, the horizontal actuator 270 is operated with respect to the test sample before the heating test to check stability, etc., of the test sample for a certain time, and then simultaneously compresses the test samples to a desired temperature and time according to a set temperature and time pattern, performing a load-coupled heating fireproof performance test. Further, when the test sample arrives at the desired temperature according to the set temperature pattern, the vertical actuator 270 is operated to lower the clamps 272 and simultaneously compresses the plurality of linear test samples Sa, performing the load-coupled heating fireproof performance test. Therefore, the vertical compression force can be simultaneously applied to the plurality of middle and long span test samples Sa to perform the fireproof performance test.

In addition, the heating furnace 100 for testing middle and long span structures in accordance with the present invention can easily apply the vertical compression force to the middle and long span structures having various sizes to perform the fireproof performance test using the vertical force applying means 250.

For example, as shown in FIGS. 7A and 7B, a vertical compression force can be easily applied to plate-shaped middle and long span test samples having various sizes to perform the fireproof performance test. Specifically, a plurality of plate-shaped test samples Sb can be mounted in the first space 132 and the second space 134 partitioned by the partition means 200 and tested therein.

In this case, as shown in FIG. 2, the plate supports 284 are installed at the plate-shaped test samples Sb, respectively. The plate supports 284 are installed at upper ends of the first space 132 and the second space 134 of the main body 110 in a state in which the cover 120 of the heating furnace 100 is removed, and the plate-shaped test sample Sb is installed at the upper part of the plate support 284 to be supported thereby, instead of the cover 120.

In this case, the lower surface of the plate-shaped test sample Sb is exposed to the first space 132 and the second space 134. In this state, the heating means 140 operates all the burners 142 disposed in the first space 132 and the second space 134 to simultaneously heat the plurality of test samples, and the exhaust means 160 exhausts an exhaust gas through the one exhaust port 162 disposed in the first space 132 and the other exhaust port 162 disposed in the second space 134.

Therefore, the plate-shaped test sample Sb is heated through the above disposition structure, and the heat is remained in the first space 132 and the second space 134, not discharged to the exterior by the plate-shaped test sample Sb.

In addition, the horizontal actuator 270 is operated with respect to the test samples to check stability, etc., of the test samples for a certain time before the heating test, and then, the test samples are simultaneously compressed to perform the load-coupled heating fireproof performance test to a desired temperature and time according to a set temperature and time pattern. Further, when the plate-shaped test sample Sb arrives at the desired temperature according to the set temperature pattern, the vertical actuator 270 is operated to lower the clamps 272 for the plate-shaped test samples and simultaneously compress upper surfaces of the plurality of test samples, performing the load-coupled heating fireproof performance test. At this time, the clamps 272 for the plate-shaped test samples can apply an equally distributed vertical load to the plate-shaped test samples Sb, more precisely performing the load-coupled heating fireproof performance test.

As described above, the vertical compression force may be simultaneously applied to the plurality of plate-shaped middle and long span test samples Sb to perform the fireproof performance test.

In addition, during the test, the size of the plate-shaped test sample Sb may be smaller than the first space 132 or the second space 134 of the main body 110. In this case, the cover 120 is covered on the first space 132 or the second space 130, which is not covered by the plate-shaped test sample Sb, to keep heat in the first space 132 and the second space 134.

Since the present invention may include the modular partition means 200, which is detachably attached to the interior of the main body, to adjust an inner volume of the heating furnace 100, the fireproof performance test of the structural member having various lengths such as 4 m, 6 m and 10 m can be readily performed. In particular, during the test, since the inner volume of the main body 110 is adjusted to perform the load-coupled heating test, it is possible to optimize consumption of various utilities required for the test.

Further, since the present invention can perform an actual material test of full scale structures such as continuous span beams and long span beams, deck plates, or bridge trusses of civil structures, deck plates for ships, and so on, having various shapes and sizes, target fireproof performance estimation of various shape conditions, which was impossible, can be performed to increase applicability of the test, precisely performing the desired fireproof performance test.

As apparent from the above description, since the heating furnace for testing middle and long span structures in accordance with the present invention has a modular structure in which the inner volume of the heating furnace can be adjusted, the fireproof performance test of the structural members having various lengths of 4 m, 6 m and 10 m can be performed. In particular, during the test, since the inner volume of the heating furnace is adjusted to perform the load-coupled heating test, it is possible to optimize consumption of various utilities required for the test.

In addition, in the case of the building, the heating furnace for testing middle and long span structures in accordance with the present invention can perform an actual material test of full scale structures such as continuous span beams and long span beams, deck plates, or bridge trusses of civil structures, deck plates for ships, and so on, having various shapes and sizes, target fireproof performance estimation of various shape conditions, which was impossible, can be performed to increase applicability of the test, precisely performing the desired fireproof performance test.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. A heating furnace for testing middle and long span structures, which comprises:
   a main body (110) having an inner wall (112) and an outer wall, wherein the inner wall is formed of a refractory material and the outer wall (114) is formed of a steel material, a detachable cover (120) installed on an open upper part thereof, and a heating space (130) formed therein;
   a heating unit (140) including a plurality of burners (142) for providing heat from two first sidewalls (w1) in a longitudinal direction of the main body (110) to heat the heating space (130);
   an exhaust unit (160) having a plurality of exhaust ports (162) for discharging an exhaust gas in the heating space (130) from two second sidewalls (w2) in a longitudinal direction of the main body (110), and exhaust pipes (166) connected to the exhaust ports (162) to discharge the exhaust gas to a chimney, respectively;
   a partition unit (200) for partitioning the heating space (130) of the main body (110) and formed of a refractory material to block transfer of heat generated from one space to the other space;
   a horizontal force applying unit (220) including a horizontal actuator (222) for applying a compression force to one side of a test sample installed in a longitudinal direction of the main body (110), and a reaction frame (232) for supporting the other side of the test sample at an opposite side of the horizontal actuator (222); and
   a vertical force applying unit (250) including a vertical actuator (270) for applying a compression force to the test sample from an upper part of the test sample installed in the main body (110), and a support frame (280) for supporting the test sample in the main body (110),
   wherein the heating space (130) of the main body (110) is partitioned using the partition unit (200) to correspond to a size of the test sample, and heat and a compression force are applied to the test sample in the heating space (130) to perform a fireproof performance test, and
   a test sample mounting space (202) is formed at the two second sidewalls (w2) in a widthwise direction of the main body (110) and an upper center of the partition unit (200), and a blocking wall (210) formed of a refractory material is disposed in the test sample mounting space (202) to open the test sample mounting space (202) according to the size of the test sample, performing the fireproof performance test.

2. The heating furnace for testing middle and long span structures according to claim 1, wherein the partition unit (200) is removed from the interior of the heating space (130) of the main body (110), the test sample is mounted to cross the heating space (130), the heating unit (140) operates the burners (142) throughout the heating space (130), and the exhaust unit (160) exhausts an exhaust gas through a plurality of exhaust ports (162) so that the test sample is heated and compressed to perform a fireproof performance test.

3. The heating furnace for testing middle and long span structures according to claim 1, wherein at least one test sample is mounted in the heating space (130) of the main body (110) partitioned by the partition unit (200), the heating unit (140) operates the burners (142) disposed in the heating space (130), and the exhaust unit (160) exhausts an exhaust gas through the exhaust ports (162) disposed in the heating space (130) so that the test sample is heated and compressed to perform a fireproof performance test.

4. The heating furnace for testing middle and long span structures according to claim 1, wherein the vertical force applying unit (250) is movable on rails (262) disposed at both sides of the bottom of the main body (110) so that the vertical actuator (270) is movable in the longitudinal direction of the main body (110).

* * * * *